United States Patent
Bennett

(10) Patent No.: US 6,833,142 B2
(45) Date of Patent: Dec. 21, 2004

(54) FORMULATION FOR THE PREVENTION AND TREATMENT OF MULTIPLE SCLEROSIS AND OTHER DEMYELINATING CONDITIONS

(76) Inventor: Duane Bennett, 18 Brookmont Dr., Wilbraham, MA (US) 01095

( * ) Notice: Subject to any disclaimer, the term of this patent is extended or adjusted under 35 U.S.C. 154(b) by 0 days.

(21) Appl. No.: 10/386,118

(22) Filed: Mar. 12, 2003

(65) Prior Publication Data

US 2004/0001899 A1 Jan. 1, 2004

Related U.S. Application Data

(60) Provisional application No. 60/363,894, filed on Mar. 14, 2002.

(51) Int. Cl.$^7$ ................................................ A01N 65/00
(52) U.S. Cl. ........................ 424/725; 424/682; 426/651; 426/656; 426/72; 514/2
(58) Field of Search ................................ 424/725, 682; 426/651, 656, 72; 514/2

(56) References Cited

U.S. PATENT DOCUMENTS 5,989,594 A * 11/1999 Cardinale Fezler ......... 424/548
6,096,737 A * 8/2000 Loder ......................... 514/217

FOREIGN PATENT DOCUMENTS

EP 0652012 A1 * 5/1993

* cited by examiner

*Primary Examiner*—Christopher R. Tate
(74) *Attorney, Agent, or Firm*—M. K. Silverman; Yi Li

(57) ABSTRACT

A method for prevention and treatment of multiple sclerosis and other demyelinating conditions is disclosed. The method includes two subsequent phases. In each phase, a patient orally administers daily a regimen which includes a specific combination of amino acids, fatty acids, vitamins and minerals. The particular regimens provide vital nutrients necessary to re-build fatty acids that may have been lost or reduced in the myelin sheathing and other locations of brain, therefore decrease one's susceptibility to multiple sclerosis and prevent reoccurrence of the disease.

8 Claims, 1 Drawing Sheet

FORMULATION FOR THE PREVENTION AND TREATMENT OF MULTIPLE SCLEROSIS AND OTHER DEMYELINATING CONDITIONS

CROSS REFERENCE TO RELATED APPLICATION

This application is a non-provisional patent application of provisional patent application Ser. No. 60/363,894 filed Mar. 14, 2002. Applicant claims the benefit of 35 U.S.C. 119(e).

BACKGROUND OF THE INVENTION +ps 1.
Area of Invention

This invention relates to the treatment of multiple sclerosis ("MS") and other demyelinating conditions.

2. History

MS is a chronic, often disabling disease of the central nervous system. Various and converging lines of evidence point to the possibility that the disease is caused by a disturbance in the immune function, although the cause of this disturbance has not been established. This disturbance permits cells of the immune system to "attack" myelin, the fat containing insulating sheath that surrounds the nerve axons located in the central nervous system ("CNS"). When myelin is damaged, electrical pulses cannot travel quickly or normally along nerve fiber pathways in the brain and spinal cord. This results in disruption of normal electrical conductivity within the axons, fatigue and disturbances of vision, strength, coordination, balance, sensation, and bladder and bowel function.

As such, MS is now a common and well-known neurological disorder that is characterized by episodic patches of inflammation and demyelination which can occur anywhere in the CNS. However, almost always without any involvement of the peripheral nerves associated therewith. Demyelination produces a situation analogous to that resulting from cracks or tears in an insulator surrounding an electrical cord. That is, when the insulating sheath is disrupted, the circuit is "short circuited" and the electrical apparatus associated therewith will function intermittently or nor at all. Such loss of myelin surrounding nerve fibers results in short circuits in nerves traversing the brain and the spinal cord that thereby result in symptoms of MS.

It is further found that such demyelination occurs in patches, as opposed to along the entire CNS. In addition, such demyelination may be intermittent. Therefore, such occurrences are disseminated in both time and space.

It is believed that the pathogenesis involves a local disruption of the blood brain barrier which causes a localized immune and inflammatory response, with consequent damage to myelin and hence to neurons.

Clinically, MS exists in both sexes and can occur at any age. However, its most common presentation is in the relatively young adult, often with a single focal lesion such as a damage of the optic nerve, an area of anesthesia (loss of sensation), or paraesthesia (localize loss of feeling), or muscular weakness. In addition, vertigo, double vision, localized pain, incontinence, and pain in the arms and legs may occur upon flexation of the neck, as well as a large variety of less common symptoms.

An initial attack of MS is often transient, and it may be weeks, months, or years before a further attack occurs. Some individuals may enjoy a stable, relatively event free condition for a great number of years, while other less fortunate ones may experience a continual downhill course ending in complete paralysis. There is, most commonly, a series of remission and relapses, in which each relapse leaves a patient somewhat worse than before. Relapses may be triggered by stressful events, viral infections or toxins. Therein, elevated body temperature, i.e., a fever, will make the condition worse, or as a reduction of temperature by, for example, a cold bath, may make the condition better.

It is the belief of the present inventor that an additional trigger in either the local disruption of the blood brain barrier, or the local response thereto is both environmentally related and related to certain serious nutritional deficiencies which, as are set forth below, particularly deplete the fatty tissue which comprises the myelin sheath, thereby increasing one susceptibility to the underlying condition. At present, there is no satisfactory treatment for MS. That is, steroids may produce a temporary improvement, however any beneficial effect invariably wears off. Clinical trials during the mid-1990s indicated that the use of interferon cannot reduce the risk of relapse. However, the effects thereof have been shown to be modest and most patients will still eventually deteriorate.

Previous researchers, most notably Chadwick (see Chadwick et al, "5, Hydroxytryptophan—Induced Myclonus in Guinea Pigs" *Journal of Neurological Sciences*, PP 157–165 (1976); Reynolds (see "MS and Vitamin $B_{12}$ metabolism," *Journal of Neuroimmunolgy*, pp 225–230, (1992); and Loder (see U.S. Pat. No. 6,096,737 (2000), entitled "Treatment of MS and other Demyelinating Conditions using Lofepramine and in combination with L-phenylalanine, Tyrosine or Tryptophanand and possibly a Vitamin $B_{12}$ Compound), all offer suggestions relative to treatment of MS.

The present invention however enjoys a primary focus of prevention of MS by those individuals believed to be, either by reason of genetics, mental state, conditions, environment, conditions of stress, or combinations thereof, to be uniquely susceptible to MS, or recurrences thereof. The present invention is also useful as a means of self-treatment by members of the public, in accordance with the specifics set forth below. This means employs a combination of non-prescription food and vitamin supplements available at most health food stores, and health and vitamin websites. Accordingly, the present invention, unlike the prior art, as represented above, does not require the use of prescription medication such as an anti-depressant, serotonin uptake inhibitor, or monoamine oxidase inhibitor with neurotransmitter inducing properties. Thus, the invention does not require the use of neuroactive prescription medication taken under the care of a physician but, rather, comprises a regimen of non-prescription food and vitamin supplements which are available to any member of the public.

This is of particular value to persons knowing or believing that, by reason of genetics, environment, stress, or empirical evidence comprising a MS marker, one is at risk for MS. While the prior art suggests the use of some of the components of the present novel method of prevention and treatment of MS such as L-phenylalanine ("LPA"), L-tryptophan, and vitamin $B_{12}$, these supplements represent but a small number of components of the aggregate of the present inventive regimen.

Otherwise, the state-of-the-art in MS research, as it is relevant to the instant invention, simply suggests the usage of the likes of LPA, L-tryptophan, and vitamin $B_{12}$, as a means of supplementing the action of a powerful nueroactive, anti-depressant prescription medications.

As is apparent, many prospective or actual victims of MS do not respond well to use of an anti-depressant and, in fact, the same may adversely impact their ability to function in life, particularly if the basis of the trigger of the MS auto-immune response does not have its basis in a psychiatrically recognized form of depression. Further, as is generally known, many individuals are allergic to antidepressants such as Lofepramine. If the MS patient is such an individual, the use of an anti-depressant may actually exacerbate the MS condition.

SUMMARY OF THE INVENTION

The regimen of the instant invention include two phases, the first of which may be in the range of 45 days to 6 months. The second of which is in the range of 1 to 7 weeks. The regimen of Phase 1 includes a combination, as is more particularly set forth below, of L-phenylalanine ("LPA"), tyrosine, and a preferred form of tryptophan (described below). The regimen also includes lecithin, choline and primrose oil. The regimen further includes vitamins in the B family, namely, vitamin $B_{12}$, niacin and folic acid. Additionally included in the regime are beta carortine, calcium and magnisium (all as are more fully described below).

In Phase 2, there is used lecithin, primrose oil and choline, as well as $B_{12}$, niacin, folic acid, beta-carotene, vitamin C, calcium and magnisium.

For the above regimen, vital nutrients necessary to re-build of fatty acids that may have been lost or reduced in the myelin sheathing and elsewhere in the brain are replaced, to thereby decrease one's susceptibility to MS or, in the case of initial symptoms, to prevent their re-occurrence.

It is in accordance with the present invention an object to re-introduce vital nutrients into the fatty tissue which surrounds and defines the myelin shield to, thereby, prevent and repair damage to the myelin sheath which may have occurred.

THE DRAWINGS

DETAILED DESCRIPTION OF THE INVENTION

Figure 1:
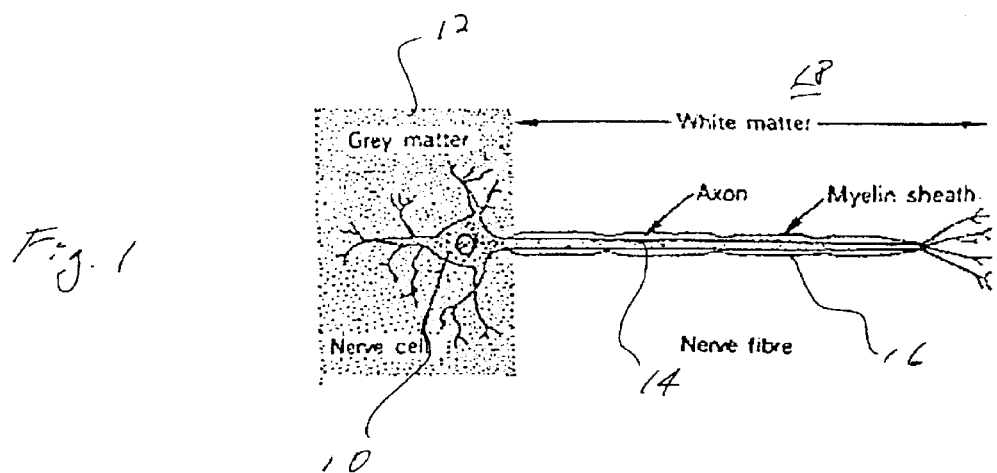
FIG. 1 is a schematic view showing a nerve cell, an axon dependent therefrom, and myelin sheathing which surrounds the axon.

As has been noted in the Background of the Invention above, evidence converging from many directions indicates that MS is caused by a disturbance in the immune function, although the reasons for such disturbance are subject to speculation. The appearance of normal myelin sheathing is shown schematically in FIG. 1. Therein, as may be noted, a nerve cell 10 with gray matter 12 of the human brain is connected by other such nerve cells by axons 14 each of which have a myelin sheath 16 which, in turn, is surrounded by white matter 18 of the human brain. This white matter, as well as the myelin sheath itself, is believed to be formed, in important part, of molecules having as their precursor, essential fatty acids including polyunsaturated fatty acids, linolieic acid ("LA"), gama-linoleic acid ("GLA") and prostaglandins.

Figure 2:
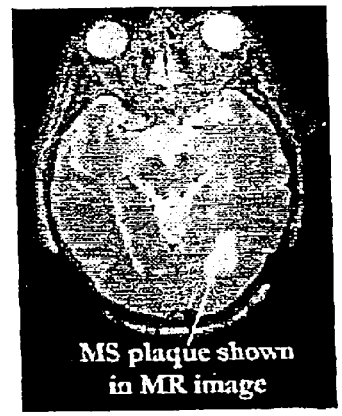
FIG. 2 is a MRI through a horizontal cross-section of the brain showing the appearance of MS-related plaque.

As may be appreciated with reference to FIG. 2, disruptions of the myelin after they have occurred, may be observed in an MRI image, as is shown in FIG. 2. Therefore, by the time a condition is so observable upon the MRI, the fragments of myelin have been destroyed such that MS related damage is probably irreversible.

The present invention provides a method of treating and/or reducing the risk of developing multiple sclerosis. The method includes two phases. In Phase 1 of the instant invention regimen, a combination of amino acids, beta-carotene, vitamin C, three B group vitamins, essential fatty acids, calcium and magnesium is employed.

It is noted that the entire Phase 1 regimen is to be taken once a day, on a full stomach, and minutes before retiring to go to bed. This regimen is to be taken for a minimum of 45 day, with a maximum period of approximately 6 months. Further, one is not to eat the following foods during the period of Phase 1 of the regimen: certain types of fresh vegetables, such as lettuce, certain types of fresh fruits, such as watermelon and apples, coffee, caffeine, alcohol, monounsaturated oil as contained in fried chicken, eggs, mayonnaise, and processed foods; butter and animal fat. However, during the treatment certain types of fresh fruits or juice and oils can be taken. Suitable examples include orange, cranberry, blue berry, sunflower oil, olive oil, grape seed oil, walnut oil, and peanut oil. No prescription medicines or drugs are to be taken during the period of administration of the below described regimen.

Phase 1

The regimen consisting essentially of the following:
A. Amino acids of the following per 100 lbs of body weight, each taken immediately before bedtime:
   L-phenylalanine (LPA)-2300 mg,
   Tyrosine-880 mg,
   Tryptophan, preferably in the form of 5-hydroxytryptophan (5-HTP)-135 mg
B. A fatty acid group consisting of the following per 100 lbs of body weight.
   Lecithin-2650 mg, including at least 925 mg of phosphatidyl choline.
   Choline in free form-660 mg
   Primrose oil-440 mg, including at least 40 mg gama-linoleic acid (GLA), and 300 mg linolieic acid (LA).
C. A group of B vitamins consisting of the following per 100 lbs of body weight:
   Niacin-220 mg
   Folic acid-35 mcg
   Vitamin $B_{12}$-2000 mcg
D. The following vitamins and minerals per 100 lbs of body weight:
   Beta-carotene-35 mg
   Vitamin C-1325 mg
   Calcium-1050 mg
   Magnesium-525 mg Choline and lecithin, both include phosphatidylcholine ("PC"). This is known as a nerve rebuilder and is an essential protector of every cell, especially those of the nervous system. PC is also a principal part of choline, an essential building block of neurotransmitters. Choline is also an essential precursor of lecithin. Further, it has been documented that choline is a nutrient which contributes to the production of myelin, the above referenced sheathing which surrounds nerve axons and other brain cells. Further, lecithin and choline/PC create an uniform support not only of the nervous system but, as well, provides benefits to many other systems such as the heart, improving the ratio between so-called good and bad cholesterol.

The role of L-phenylalanine (LPA), tyrosine and tryptophan relative to neurological health and a general sense of well being as a counter to depression has been well documented. Accordingly, tryptophan, tyrosine, and LPA comprises the most effective known combination of amino acids for the combat of depression, this in distinction to the use or neuroactive prescription drugs of the type suggested by Loder above.

The B vitamins as a group and, specifically, niacin, folic acid and $B_{12}$ have an inherently beneficial effect upon the central and peripheral nervous system. Injections of vitamin $B_{12}$ have long been used in the treatment of neurological disorders inclusive of MS, Alzheimers, Lou Gehrig's disease and other memory-related conditions. Further, and of particular significance relative to the immune response theory of MS, is the fact that individuals with demyelinating diseases do not properly metabolize Vitamin $B_{12}$, thereby leaving them more vulnerable to nerve damage. Further, when $B_{12}$ is not properly metabolized, a higher than average level of homocysteine will appear which, it has been established, is a characteristic of an auto-immune malfunction in MS victims.

$B_{12}$ is also known to work in combination with folic acid to control homocysteine levels to thereby decrease the risk not only of MS but, as well, heart disease and osteoporosis. It is, thereby, to be appreciated that the present inventive regimen is of value not only with specific reference to MS but, as well, to a broad spectrum of diseases and conditions which flow from deficiencies of the amino acids, B vitamins, fatty acids, and the minerals suggested herein.

Phase 2

With reference to Phase 2 of the instant regimen which, typically, may be initiated at anytime between six weeks and six months after the start of Phase 1, this is as follows:

One-half of the below set forth quantities, per 100 pounds of body weight, are to be taken one hour before bedtime and the balance at bedtime upon a full stomach.

Lecithin-2100 mg, inclusive of PC of 740 mg.

Primrose oil-450 mg, inclusive of GLA of 40 mg and LA of 300 mg.

Choline-1325 mg in free form $B_{12}$-2650 mcg

Niacin-220 mg

Folic acid-700 mcg

Beta-carotene-35 mg

Vitamin C-2000 mg

Calcium-4400 mg

Magnesium-2200 mg

The period of Phase 2 is 1 to 7 weeks.

EXAMPLE

Before taking the regimen, the patient continually feeling heavy twitching throughout his body, and loud buzzing in the ears. The head was affected by many different food intakes; and his vision was blurred. There was confusion, memory loss, and numbness in the hands and feet.

After taking the regimen, the patient felt renewed. All of the following issues were reduced and eventually eliminated: heavy twitching throughout the body, loud buzzing in the ear, bad effects by many different foods intakes, blurred vision, confusion and memory loss. All of these stopped upon taking the regimen. Numbness in the hands and feet was substantially reduced, although still present.

It is believed that the above described regimen is particularly effective with respect to persons living in urbanized areas or areas in which greater concentration exists of herbicides, pesticides and other toxins, the result of which, in the absence of treatment, is believed to be a reduction in the brain fat of central part of the myelin sheath of nerve axons. This is believed to be documented by the fact that people living in naturally healthier environments do not suffer the same instance of MS as do those are exposed to such environmental hazards.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

I claim:

1. A method of treating and/or reducing the risk of developing multiple sclerosis comprising the steps of:
   (i) orally administering to a subject in need thereof a first regimen once daily before bedtime in a Phase 1 period, said first regimen consisting essentially of:
      (a) amino acids in amount per 100 lbs of body weight consisting of:
         2300 mg of L-phenylalanine,
         880 mg of tyrosine, and
         135 mg of tryptophan; and
      (b) a group of fatty acids in amount per 100 lbs of body weight consisting of:
         2650 mg of lecithin.
         660 mg of choline, and
         440 mg of primrose oil; and
      (c) a group of B vitamins in amount per 100 lbs of body weight consisting of:
         220 mg of niacin,
         35 mcg of folio acid, and
         2000 mcg of vitamin $B_{12}$; and
      (d) a group of vitamins and minerals in amount per 100 lbs of body weight consisting of:
         35 mg of beta-carotene,
         1325 mg of vitamin C,
         1050 mg of calcium, and
         525 mg of magnesium; and
   (ii) thereafter orally administering to said subject a second regimen daily in a Phase 2 period, said second regimen consisting essentially of:
      2100mg of lecithin,
      450 mg of primrose oil,
      1325 mg of choline,
      2650 mg of $B_{12}$,
      220 mg of niacin,
      700 mcg of folic acid,
      35 mg of beta-carotene,
      2000 mg of vitamin C,
      4400 of calcium, and
      2200 mg of magnesium.

2. The method of claim 1 further comprising administering said second regimen in two doses, wherein one half of said second regimen is administered about one hour before bedtime and another half of said second regimen is administered at bedtime with a sufficient amount of food.

3. The method of claim 2, wherein said Phase 1 period is from forty five days to six months.

4. The method of claim 3, wherein said Phase 2 period is from about one to about seven weeks.

5. The method of claim 1, wherein said tryptophan is 5-hydroxytryptophan.

6. The method of claim 1, wherein said lecithin contains 740 mg of phosphatidyl choline.

7. The method of claim 1, wherein said primrose oil contains 40 mg gama-linoleic acid, and 300 mg linoleic acid.

8. The method of claim 1, wherein said choline is in free form.

* * * * *